(12) United States Patent
Boehringer et al.

(10) Patent No.: US 6,264,890 B1
(45) Date of Patent: Jul. 24, 2001

(54) METHOD AND APPARATUS FOR COLLECTING AND PROCESSING BLOOD

(75) Inventors: John R. Boehringer, Wynnewood; John Karpowicz, Chester Springs; Sean Kerr, Collegeville; Christopher L. Radl, Philadelphia, all of PA (US)

(73) Assignee: Boehringer Labiratories, Inc., Norristown, PA (US)

( * ) Notice: Subject to any disclaimer, the term of this patent is extended or adjusted under 35 U.S.C. 154(b) by 0 days.

(21) Appl. No.: 09/197,620

(22) Filed: Nov. 23, 1998

Related U.S. Application Data

(63) Continuation of application No. 08/783,572, filed on Jan. 15, 1997, now Pat. No. 5,879,624.

(51) Int. Cl.[7] .......................... A61M 1/14; A61M 37/00; A61M 39/00; F04B 43/08
(52) U.S. Cl. .................. 422/44; 604/4.01; 604/5.01; 604/6.01; 604/35; 417/474; 137/802
(58) Field of Search ................ 604/4, 35, 5–6; 137/802; 417/474; 422/44

(56) References Cited

U.S. PATENT DOCUMENTS 4,631,050    12/1986    Reed et al. .

(List continued on next page.)

FOREIGN PATENT DOCUMENTS

| 0 155 003 | 9/1985 | (EP) . |
|---|---|---|
| 0 313 348 | 4/1989 | (EP) . |
| 0 432 897 A2 | 6/1991 | (EP) . |
| 0 554 460 A1 | 8/1993 | (EP) . |
| 0 620 017 A2 | 10/1994 | (EP) . |

OTHER PUBLICATIONS

Haemocell System 350, Haemocell, Inc., 77 Accord Park Deive, Norwell, MA 02061.
Autotransfustion of Whole Blood in Massive Bleeding, Jan Otto Solem, et al, Acta Chir Scand 152:427–432, 1986.

(List continued on next page.)

*Primary Examiner*—Angela D. Sykes
*Assistant Examiner*—Ron Harris, Jr.
(74) *Attorney, Agent, or Firm*—Paul & Paul

(57) ABSTRACT

A container is provided that is disposable, for first collecting blood delivered from a patient, preferably by a vacuum draw of blood into a container, and then the blood in the container is treated. The treatment is provided by an at least partial a back-and-forth or reciprocating motion of blood along membranes, such that filtrate components of the blood pass through the membrane walls and are collected, whereby retentate components of the blood are retained, with the back-and-forth motion being provided by a substantially constant vacuum draw, that provides a pumping action by a diaphragm pump. A replenishment liquid is automatically added, substantially proportional to the amount of filtrate components of the blood that are withdrawn. The membranes are protected by a device which removes body fat or other potentially harmful materials. Various automatic techniques are also supplied to control the amount of replenishment liquid being added, and the amount of retentate components of the blood that are retained. Various safety features are also provided.

7 Claims, 5 Drawing Sheets

U.S. PATENT DOCUMENTS

| | | |
|---|---|---|
| 4,670,147 | 6/1987 | Schoendorfer et al. . |
| 4,758,238 * | 7/1988 | Sundblom et al. .................. 604/319 |
| 4,790,942 | 12/1988 | Shmidt et al. . |
| 4,828,543 | 5/1989 | Weiss et al. . |
| 4,935,002 | 6/1990 | Gordon . |
| 5,053,140 | 10/1991 | Hurst . |
| 5,167,817 | 12/1992 | Bellhouse . |
| 5,203,778 * | 4/1993 | Boehringer et al. ................. 604/317 |
| 5,242,384 | 9/1993 | Robinson et al. . |
| 5,362,406 | 11/1994 | Gsell et al. . |
| 5,378,227 | 1/1995 | O'Riordan et al. . |
| 5,423,738 | 6/1995 | Robinson et al. . |
| 5,639,376 | 6/1997 | Lee et al. . |
| 5,725,775 * | 3/1998 | Bene et al. ........................... 210/646 |
| 5,957,137 * | 9/1999 | Dalke et al. ......................... 128/898 |
| 6,017,493 * | 1/2000 | Cambron et al. ...................... 422/44 |

OTHER PUBLICATIONS

A new Method for Autotransfusion of Shed Blood, Jan Otto Solem, et al, Acta Chir Scand 152: 421–425, 1986.

Membrane Plasma Separation and the On–Line Treatment of Plasma by Membranes, T. Malchesky, 1989, Elsevier Science Publishers B.V.

Microporous Membrane Filtration for Continuous–Flow Plasmapheresis, Barry A. Solomon, et al, pp. 489–505.

Innovative Processes for Membrane Plasma Separation, M.Y. Jaffrin, Journal of Membrane Science, 44 (1989) 115–129, Elsevier Science Publishers B.V., Amsterdam.

Filtration Plasmaphersis in VIVO, T.B. BWiltbank, et al, Transfusion, Sep.–Oct. 1981, vol. 21, No. 5.

Plasma Exchange Therapy, International Symopisum Wiesbaden, 1980, F. Castino et al.

* cited by examiner

METHOD AND APPARATUS FOR COLLECTING AND PROCESSING BLOOD

CROSS-REFERENCE TO RELATED APPLICATION

This application is a continuation of application Ser. No. 08/783,572 now U.S. Pat. No. 5,879,624 filed Jan. 15, 1997.

BACKGROUND OF THE INVENTION

It is known in the art of treating blood, that blood may be collected and filtered, whereby bone fragments and other debris in the blood may be removed from the blood, with the blood then being returned to the patient for infusion. An example of such a process and apparatus is disclosed in U.S. Pat. No. 4,781,707, the complete disclosure of which is herein incorporated by reference.

It is also known to remove insoluble fats (or lipids) from blood prior to re-transfusing the blood to a patient. Examples of such techniques are disclosed in U.S. Pat. Nos. 5,203,778 and 5,354,262, the complete disclosures of which are likewise herein incorporated by reference. Other examples of blood treatment for re-use of the blood reside in U.S. Pat. No. 5,133,703, the complete disclosure of which is also herewith incorporated by reference.

It is also known that, prior to infusion of blood to a patient, one may remove certain components of the blood, for example, by centrifuge techniques, for infusing the remaining blood or plasma to the patient. Examples of substances that might be removed from the blood before the blood is re-transfused to the patient might be saline, proteins, and other substances that are not desired to be infused in quantity. Such substances might also include surgical irrigants, pharmaceuticals, extracellular proteins, bile, gastric fluids, fat liquids and fat particles, cellular debris, blood clots, clumped cells, tissue, coagulation byproducts, cancer cells or other potentially harmful substances. The removed components may be passed to waste. Upon reintroduction of the more greatly desired components of the blood, it is often preferable not to reintroduce some components so the available centrifuge or other separation techniques may serve to separate some components from that portion of the blood that is to be infused to a patient. Various other separation techniques have also been used to separate some components of the blood from others before returning the desired components of the blood to a patient for re-transfusion. Many of the existing techniques for separating various components of the blood prior to returning the desired components of the blood to a patient, involve large, expensive equipment and specialized technicians to operate it, including but not limited to centrifuge type equipment and the like, whereby treating physicians may find that such equipment is in use by others when they desire to use the same for their own patient, and consequently it may occur that where separation of blood components is desired such might not occur due to the unavailability of the equipment for use. In other circumstances, because of the cost of the equipment for doing the blood separation, hospitals might not have such equipment on hand, and again, the desired separation of various components of the blood may not occur prior to infusion. Existing membrane systems have been unsuccessful due to fouling and lack of speed. They are typically used for small laboratory sample quantities. Such are generally of the centrifugal washer type. In some situations, as for example in emergencies, the capacity and speed of single centrifugal washers may be limited.

The present invention is directed toward providing simple, low-cost, single use disposable collection and processing equipment and a method of providing and using the same, whereby many units of such equipment may be maintained, readily on hand at a hospital or the like, for single use and then to be discarded.

The present invention allows running a number of units or cell washers together, for example, arranged in parallel.

The present invention is also directed to providing blood separation techniques whereby microporous membranes may be used to treat the blood and membrane protection devices are used to protect the membrane. The treatment can reside in separation from the red blood cells those components of larger and smaller size, including the more watery components. Optionally, the treatment of the blood can reside in delivering other substances to the blood.

The present invention is also directed toward providing a novel filter, for independent use, as well as for protecting a microporous membrane that is to be used for processing blood, from being fouled, which prior art techniques have had difficulty in protecting, and to maintain clinically acceptable speed of separation.

The present invention is also directed toward providing a novel pump, for independent use as well as for recirculating blood along a microporous membrane.

The present invention is also intended for processing under conditions of minimum blood volume as well as under conditions in which a minimum volume is lost or captured in the filter (hold-up volume). Thus, the present invention is practical for pediatric and small blood loss cases which are problems which plague the centrifuge type systems, because of their large holdup (wasted) blood volumes.

SUMMARY OF THE INVENTION

The present invention provides a single-use, inexpensive, disposable collecting and processing system in which liquid from or to be delivered to a body, such as blood is treated prior to, during, or after removal from a patient, prior to infusion to the patient, and in which the blood treatment is effected, including an at least partially oscillating or to-and-fro motion of the blood, preferably along microporous membrane surfaces, through which the treatment takes place.

Accordingly, it is a primary object to provide novel method and apparatus for collecting and/or processing blood for autotransfusion, wherein the entire apparatus is relatively inexpensive, for single use, and intended to be disposable.

It is another object of this invention to accomplish the above object, in which microporous membranes are used to accomplish separation of components of blood from the remainder of the blood.

It is another object of this invention to provide a novel filter for independent filtration of fat and debris or for use with a blood processing membrane for protecting the membrane from fat and debris, whether the fat and debris is larger or smaller than red blood cells.

It is a further object of this invention to accomplish the above objects, in which the blood passes along the microporous membranes in a motion that is best described as at least partially back-and-forth motion, by using a unique pump that does not operate via centrifugal or peristaltic motion, that prevents damage to red blood cells.

It is a further object of this invention to accomplish the above objects, wherein the blood processing is accomplished via a novel diaphragm pump.

It is a further object of this invention to accomplish the above objects, in which the blood processing is accomplished via a partial-vacuum-operative, preferably substantially constant vacuum pump.

It is a further object of this invention to provide a blood processing system which incorporates automatic controls, in order to minimize the skill required for operation.

It is a further object of this invention to minimize the hold-up volume of blood during blood processing.

It is yet another object of this invention to process blood under conditions which minimize the required volume of blood that is necessary for processing.

Other objects and advantages of the present invention will be readily apparent to those skilled in the art from a reading of the following brief descriptions of the drawing figures, the detailed descriptions of the preferred embodiments, and the appended claims.

BRIEF DESCRIPTION OF THE DRAWING FIGURES

Figure 1:
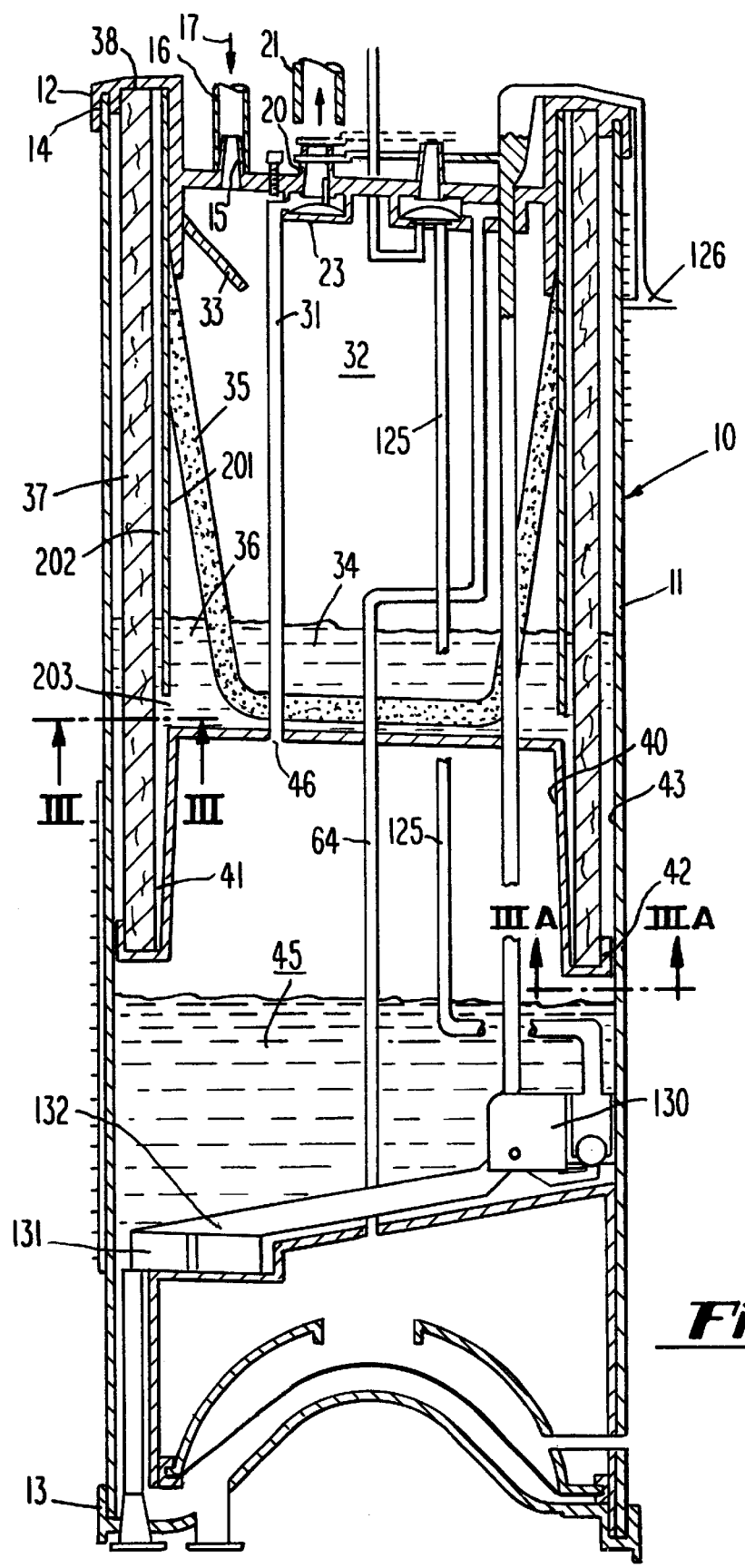
FIG. 1 is a schematic vertical sectional view of a generally cylindrical blood collection apparatus of this invention, generally in a collection mode, for collecting blood from a patient for later infusion to the patient, which illustration also discloses a means for processing collected blood.
Figure 3:
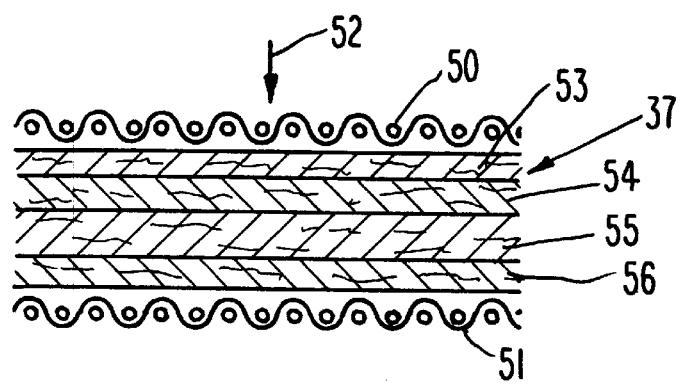
FIG. 3 is an enlarged transverse sectional view, taken generally along the line III—III of FIG. 1, and wherein the filter, generally a fat filter of this invention is shown in greater detail.
Figure 3A:
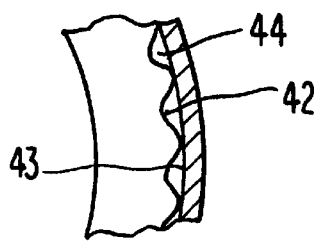

FIG. 3A is an enlarged transverse sectional view, taken through the wall of the collection container of this invention, beneath the bottom cap of the filter, and wherein the corrugated nature of the bottom cap, is shown alternately engaging and non-engaging the inner wall of the cylindrical collection chamber is illustrated, whereby blood that passes through the filter of FIG. 3 is free to pass into the upper collection chamber of FIG. 1.

Figure 4:
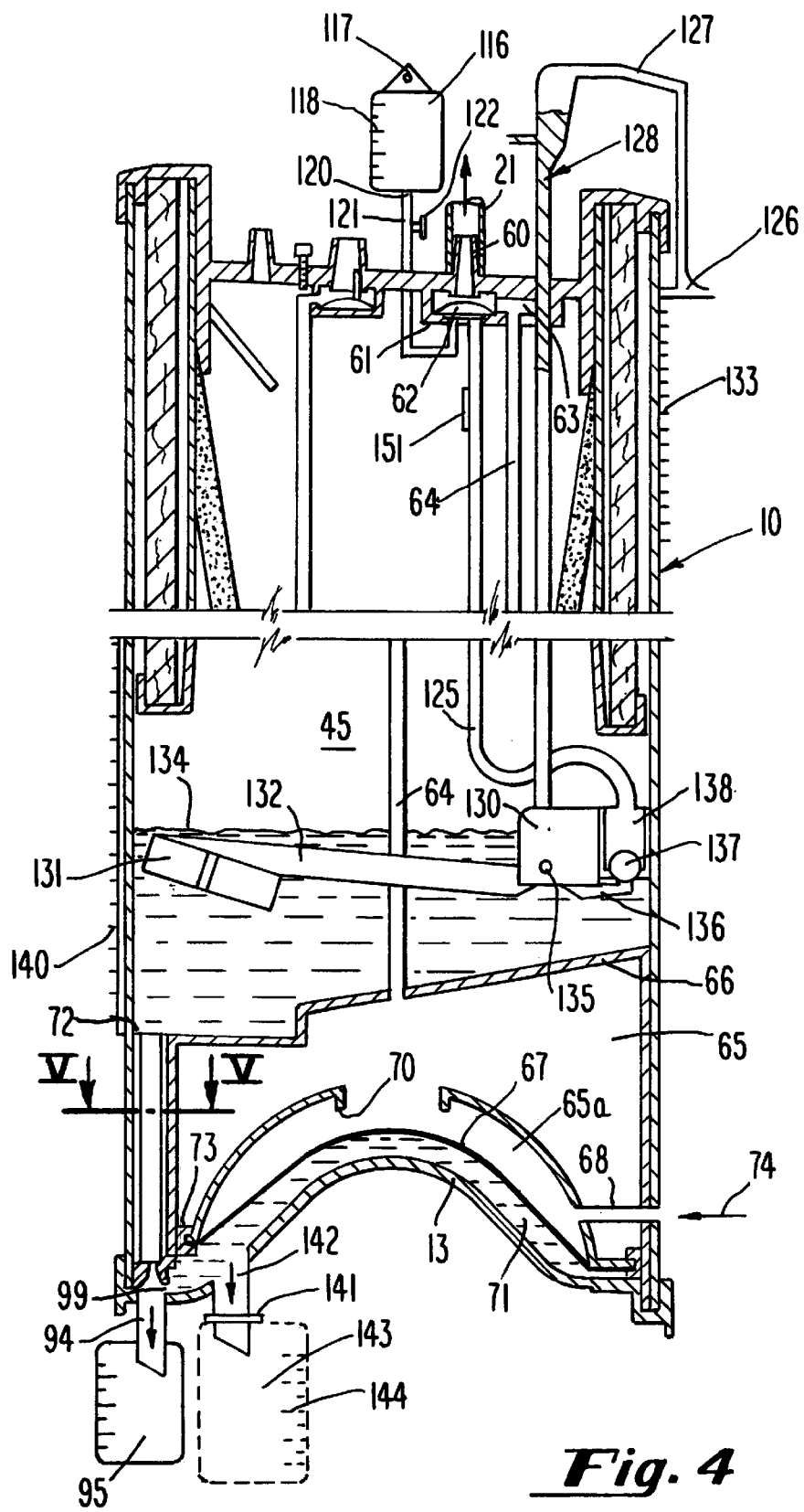

FIG. 4 is a schematic vertical sectional view, taken through the cylindrical collection and processing chamber of this invention, with various other components of the blood processing system being also illustrated, with the apparatus of FIG. 4 being shown in the blood processing mode, and with certain central portions of the illustration being fragmentally broken away for the sake of clarity.

Figure 5:
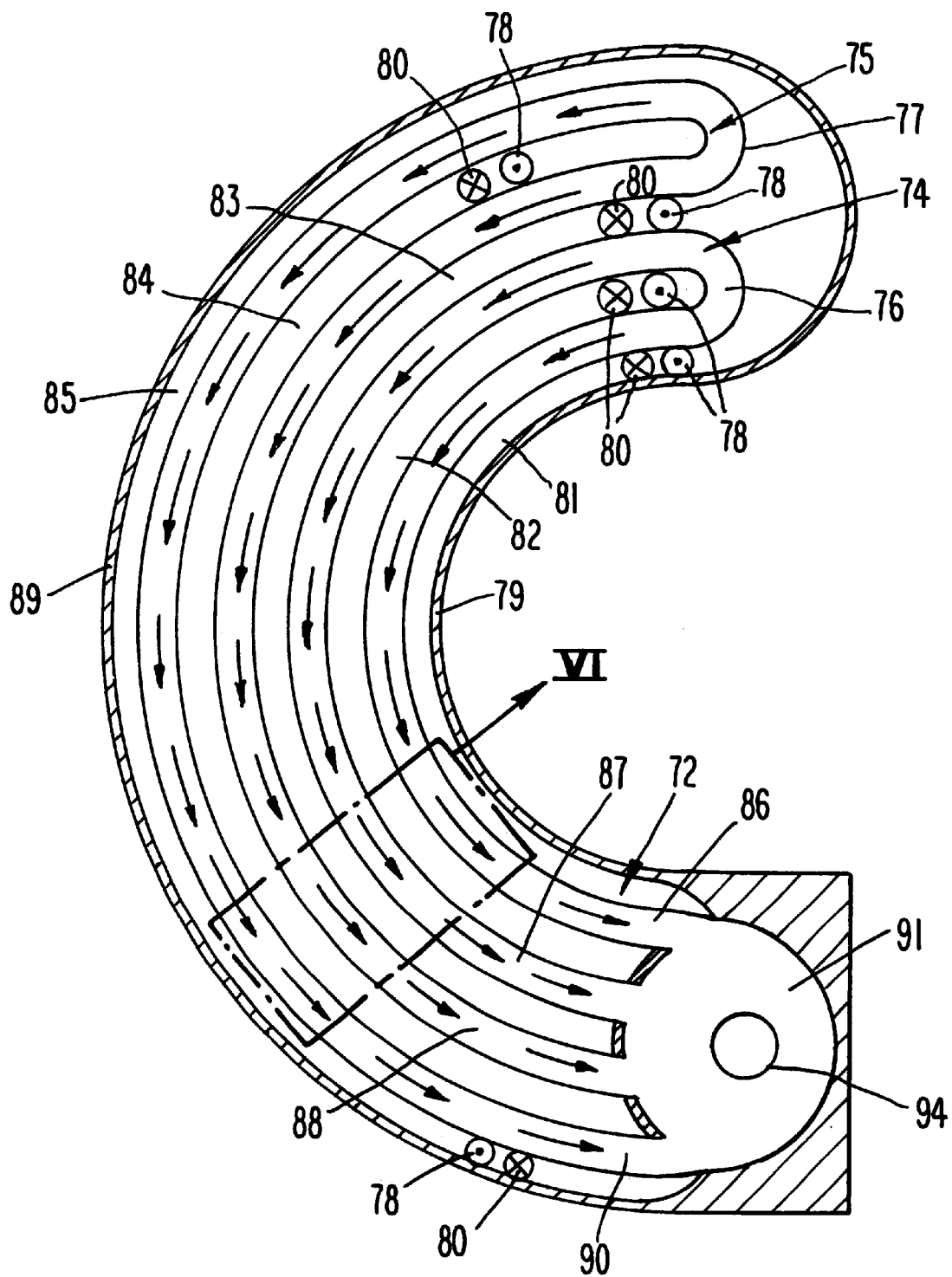

FIG. 5 is an enlarged transverse sectional view, taken through the membrane stack of the blood processing apparatus of FIG. 4, generally along the line of V—V of FIG. 4, and wherein the flow of membrane-separated components of the blood is illustrated as they pass toward waste collection.

Figure 6:
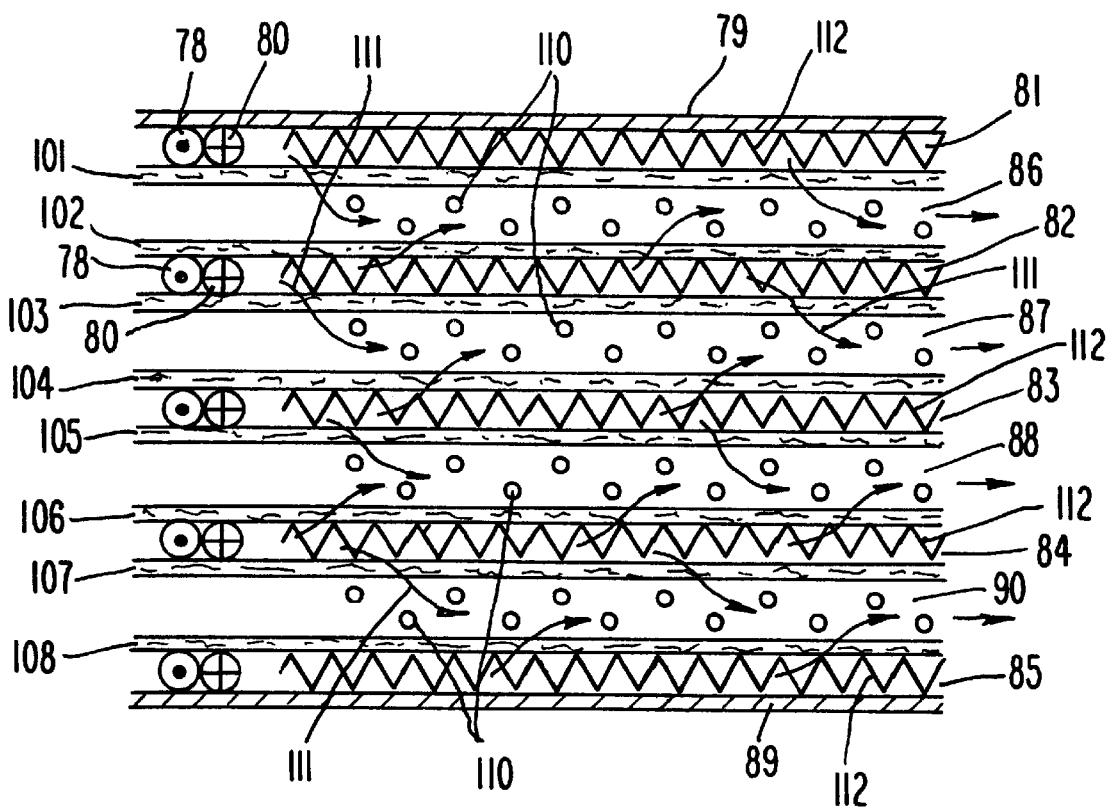

FIG. 6 is a schematic enlarged, detail view of the membrane stack shown in FIG. 5, fragmentally illustrated, and with the to-and-fro motion of blood being illustrated into and out of the plane of the paper, and with the flow of waste components of the blood along membranes also being illustrated.

DETAILED DESCRIPTIONS OF THE PREFERRED EMBODIMENTS

Referring now to the drawings in detail, reference is first made to FIG. 1, wherein there is illustrated a blood collection and processing apparatus in accordance with this invention, generally designated by the numeral 10.

The collection device 10 includes a preferably vertical cylindrical wall 11 and upper and lower end caps 12 and 13, respectively, closing off the ends. The upper end cap 12 is provided with a generally cylindrical slot 14, adapted to receive the upper end of cylindrical wall 11 therein, as shown, for sealing close the upper end of the cylindrical wall 11. The lower end cap 13 is similarly engaged with cylindrical wall 11.

The end cap 12 is provided with a nipple-type blood inlet 15, over which is disposed a blood inlet conduit 16 for receiving blood therein in the direction of the arrow 17. The blood in the conduit 16 may be connected to an aspiration or suction device of a suction tip type, such as a wand (not shown) that, in turn, scavenges blood from a patient either during an operation, or post- operatively, or the conduit 16 may be connected to a blood drainage line from a patient, such as for example, during the post-operative condition of the patient. If a wand is used to collect blood for provision through the conduit 16 such may be constructed in accordance with various techniques, including but not limited to that set forth in U.S. Pat. No. 5,120,305, the complete disclosure of which is herein incorporated by reference.

Figure 2:
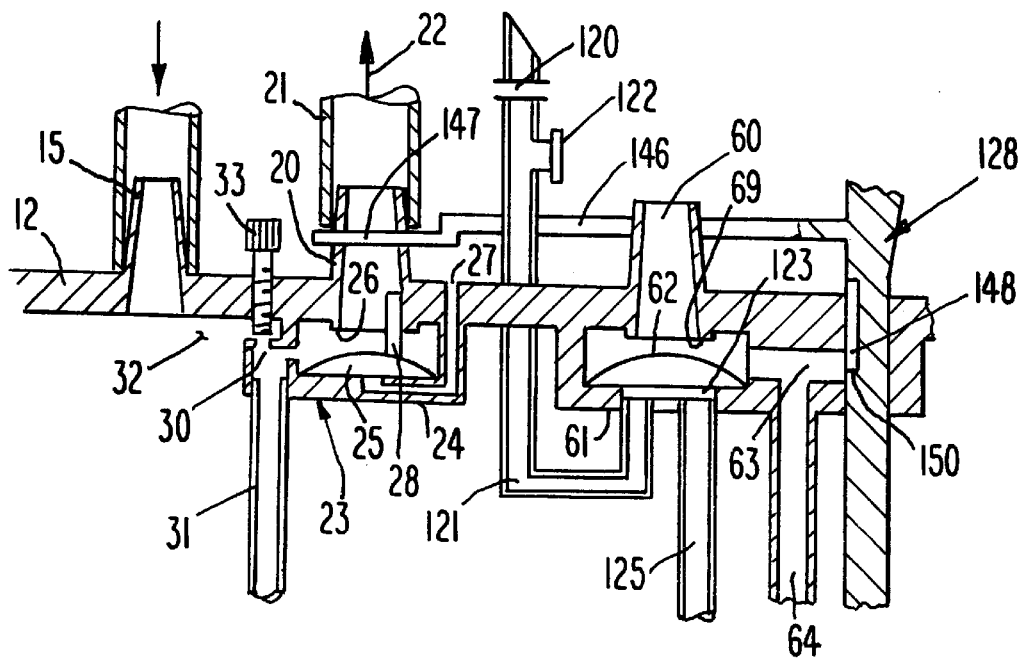
FIG. 2 is an enlarged, fragmentary vertical sectional view, taken through the upper end of the container for collecting blood as shown in FIG. 1, wherein various connection and valve components are more clearly illustrated.

A generally nipple-like vacuum connect port 20 is disposed in upper end cap 12, for connection of a vacuum conduit 21 thereover, for drawing air through the port 20 in the direction of the arrow 22 of FIG. 2. Preferably, the source of vacuum applied at 21 is a constant source of vacuum as, for example, provided via a hospital vacuum supply, or the like, although the source of vacuum could be supplied by other means, such as from a battery operated pump, an emergency vehicle, or any other vacuum source, either constant or variable. Preferably the vacuum supplied via conduit 21 will be in the range of 300–500 mm Hg.

A switch 23 is shown below the vacuum port 20, for regulating the vacuum provided from line 21, to some desirable level, such as, perhaps, 150 mm Hg. The switch 23 includes a housing 24 and a flexible generally elastomeric diaphragm 25 which flexes upwardly to close against valve seat 26, when a predetermined vacuum shut-off level is reached, with an air vent 27 communicating with the lower side of the diaphragm 25 to enable the diaphragm to have upward motion. A dampening rod 28 is carried by the diaphragm 25, for providing a dampening function, in order to retard or eliminate vibration that might result from drawing a vacuum through the switch 23. The dampening rod 28 may be a vertical, elastomeric coated rod, adapted to rub against the inter cylindrical wall of the port 20, to provide a desired dampening function.

There may be instances where blood collection to device 10 is by other means than vacuum, such as, for example, by gravity or under conditions of light pressure or pumping. For example, blood may be delivered to the unit 10 from a sealed collection receptacle, from a closed body cavity, from a blood bag or the like, in which the blood may be supplied directly to the port 15.

While vent 30 in vacuum transfer tube 31 is normally open, to draw a vacuum in blood fill zone 32, the vent orifice 30 may be occluded by external means, such as by the generally hand-operated screw 33, threaded into end cap 12, just above the orifice 30, for closing the same when blood is to be delivered to the blood fill zone 32 from a sealed collection receptacle, closed body cavity, or the like.

As blood enters the inlet port 15, it will first encounter a splash guard 33, for deflecting blood away from the area immediately surrounding the port 15 within the blood inlet zone 32, to go to the bottom of said zone 34, within clot filter 35. This prevents a spray caused by blood entering the unit from drying on the inside of the clot filter 35 and inhibiting or shutting off operation of the filter 35. The clot filter 35 removes coarse debris from the blood, such as bone chips and the like, and allows the remaining blood to pass through, to zone 36, on the other side of the filter 35.

A fat filter 37, generally hollow and cylindrical in construction, is captured at its upper end in end cap 12, at 38, and at its lower end in filter bottom cap 40, specifically, within channel 41 thereof. In cross-section, as shown in FIG. 1, the filter bottom cap 40 is of inverted U-shaped section as shown, the lower end of which, has at its periphery, a corrugated upturned flange 42, better seen in the detail of illustration 3A, with the outer periphery of the corrugated flange 42 in friction-fit engagement against the inner surface 43 of the cylindrical wall 11 of the collection device, providing a plurality of passageways 44 for passage of blood into the upper chamber 45, as shown in FIG. 1, after passing through the fat filter 37.

The fat filter 37 removes insoluble oils and particulate fat, some platelets, some of the white cells, many small fat particles below 4 $\mu$m in size, bone particles, tissue, clumped cells and microaggregates, from the blood. Generally, insoluble oils are essentially triglycerides in liquid form. Particle fat is characterized as a lipid vesicle with a protein skin and ranges in size from below one micron to larger than 40 microns. Oils and small particles of this type generally have a tendency to significantly foul and disable membranes and the use and structure of filter 37 provides a highly significant improvement against membrane fouling.

When a vacuum is drawn via vacuum port 20, via transfer tube 31, vacuum is drawn on the upper chamber 45 because the transfer tube 31 communicates through the bottom cap 40 at 46.

When blood is being drawn into the zone 32 via port 15, the presence of blood in the line 16 and through the port 15 increases the suction pressure in chamber 32 via the transfer tube 31, such that the pressure drop across the filter 37 is slight, perhaps on the order 10 mm Hg. However, often, the drawing of blood through the port 15 is intermittent, as for example, when a wand is being used to draw blood from a wound, or in other instances the supply of blood is non-constant for any of various reasons. In such situations, air is drawn through the port 15 more rapidly, and in such a situation the pressure drop across the filter 37 automatically increases substantially, sometimes on the order of 120 mm Hg, in which situation there is automatically much more blood flow across the filter 37 and into the zone 45.

With reference to FIG. 3, a cross-section of the fat filter is seen to comprise support screens 50 and 51 on opposite sides thereof, also cylindrical in configuration, sandwiching therebetween a plurality of other layers. The flow of blood is shown in the direction of arrow 52 in FIG. 3, which represents blood flow from the zone 32, into the zone 45 of FIG. 1, in some cases rising in narrow space 202 defined by outer cylindrical surface of cylindrical baffle 201 and inner peripheral surface of the fat filter 37, as shown in FIG. 1. This narrow space 202 is substantially coextensive with said cylindrical and peripheral surfaces to minimize fiber clogging through blood accumulation on the inner peripheral surface of the fat filter 37 during high blood flow between the pre-filter chamber 32 and post-filter chamber 45 by enhanced uniform distribution of blood flow to the filter peripheral surface. The support screen 50 distributes blood along the fluid entry surface of filter 53, which will preferably be a polyester pre-filter having a pore size preferably within the range of 20 $\mu$m–100$\mu$, for removal of fine debris, microaggregates, clumped cells and smaller clots and some fat. A $\mu$m=$10^{-6}$ meters. Next, a fat reservoir 54, which may be constructed of polypropoylene layers having a pore size preferably in the range of 30 $\mu$m–100$\mu$ and of relatively low surface tension and removes primarily the insoluble liquid triglycerides. Next, the blood encounters the particle fat filter 55, which is preferably of polyester construction, having an effective pore size preferably in the range of 5 $\mu$m–25$\mu$. This filter 55 is optimally constructed by layering from one or more layers of a melt blown polybutylene terapthalate material. Melt blowing provides the smallest fiber diameter (as low as one micron) which serves to maximize surface area for absorption or adhesion and/or adsorption of fat particles and other potentially harmful substances. Additionally, thin layers of 54 and 55 can be interleaved to yield alternating layers of fine and coarse pore size as well as alternating hydrophilic and lipophilic layers, which enables effective particle and liquid fat removal. A hydrophilic layer is one having a surface with a wetting surface tension greater than 48 dynes/cm and a hydrophobic layer is one having a surface with a wetting surface tension less than 48 dynes/cm. Then, the blood passes through retention layer 56 and out through screen 51. The retention layer 56 is constructed of a polyester fiber which ensures that free fibers are maintained within the filter bed and transport screen 51 is enabled to provide structural rigidity and convey filtered blood along the outside of the filter. The layer 56 may be on the order of a pore size of 80 $\mu$m, and is preferably with a range of 20$\mu$ to 200$\mu$. It is recognized that a fat and debris filter will become progressively occluded during the course of collection. Certain features of the present invention serve to ensure that an optimum amount of filter surface will be employed as fluid flow rates change and that the volume of blood which can be retained by completely occluded portions of the filter is minimized.

With reference to FIG. 1, it will be noted that the bottom cap 40 is in the shape of an inverted dome, and forms a narrow channel 41 between itself and the lower inner cylindrical wall of the fat filter 37. In low flow operation, the fat filter is able to maintain a low blood level in zone 36, more or less as shown in FIG. 1, or at or below the annular opening 203 below the cylindrical baffle 201. During periods of high flow, or as fat filter 37 becomes progressively occluded from the bottom upward, the level of blood in zone 36 rises to the top of opening 203. Blood is then drawn up into the annular space 202 formed circumferentially outside the baffle 201. The hold-up volume of blood can never exceed that which is established by the annular spaces 41 and 202, even with a fully occluded filter. It will be apparent that the size, such as height, of the annular opening 203 can be varied, by various designs, to suit numerous clinical conditions that may arise. It will be apparent that hold-up volume of blood is significant, and is desired to be minimized, because it wastes red blood cells that cannot be returned to the patient. Also, it is significant that a minimum volume of blood is required for processing in accordance with the processing mode of this invention as is discussed hereinafter, principally in connection with FIG. 4, because in cases of small blood loss, for example, in treating pediatric patients, the ability to process blood with a minimum volume of blood can be especially important.

Processing as described herein involves the separation of blood components via tangential flow of blood in a membrane array. The combination of flow along a membrane surface and turbulence inducing spacers serves to discourage formation of retained components on the membrane which can impair flow of material across the membrane. Upon generation of a transmembrane pressure, flow can be effected through the membrane. Additionally, the turbulence inducing spacers enable the membranes to be separated significantly beyond that which has been previously disclosed. This reduces resistance to blood flow and enables higher blood flows for a given size pump.

The filter 37 performs a significant function as a membrane protection means, in preventing the fouling, or plugging of the pores of the membranes that will be discussed hereinafter for separating plasma from blood cells. For example, the filter can protect the membrane in such a way that the filter may pass cellular components of blood, on the order 4–8 $\mu$m in size, such as red blood cells, but at the same time capture small particles predominantly of fat, some of which are surrounded by protein skins and are many times smaller than the red blood cells. Such has not heretofore generally been recognized in the art as comprising a serious fouling condition in attempts to process red blood cells. Furthermore, there is liquid fat present in much larger globules and possibly quantities, which must be removed not only to protect the membrane, but also to protect the patient; i.e., to keep such globules out of blood that is to be infused to the patient. When membranes are unprotected by filters, they will cease to be effective in processing the blood, and will tend to shut down by plugging, especially in the presence of clotting, fat and debris. While such occurrences may take place in trauma and treatment or orthopedic collection, they are not limited to such occasions. The present fat filter has been found to be effective in protecting the membrane. Other measures have been effective in protecting the membrane from fouling. For example, any reversal of pressure or flow on the membrane serves to dislodge retained components from the membrane surface. A random or controlled periodic back pulse of pressure on waste conduit 94 serves to enhance waste flow through the membrane by blowing off membrane surface contaminants. Pressure or flow reversal can also be accomplished in a dynamic sense such as that which is caused by the pumping action itself wherein a small amount of compliance in the membrane assembly enables the membrane to track or move with the cycling of the pump. For example, on the pump fill stroke the membrane expands slightly into the blood and separating screens and on the subsequent out stroke, the membrane is forced out to the support screen. With slight resistance to flow in conduit 94, the membrane can be thought of to move through a briefly stationary fluid, thus dynamically clearing its surface. Detergent additives to the blood, for example polysorbate 80, enhance flow by reducing the surface tension of the waste fluid, which increases flow in the membrane pores at a given pressure.

The membrane may be protected from fouling through the use of sound energy as well. Sound energy is another form of pressure and it can be utilized to excite the membrane surface similar to a pressure back pulse on conduit 94. An ultrasonic emitter can be incorporated into conduit 94. The fluid in conduit 94 would serve to transmit the sound energy to the membrane itself and impose vibrations. These vibrations would serve to discourage fouling of the membrane surface.

Alternately, the energy source could be attached directly to the membrane itself. An additional option would be to excite the blood directly.

The mechanism whereby the filter is capable of removing particles of fat smaller than the effective pore size may be related to surface chemistry of PBT fibers. It is anticipated that these surfaces can be optimized for more effective fat removal as well as being specifically treated for other potentially harmful substances or cells.

As can be seen from the above, the apparatus 10 in accordance with this invention has been described as collecting blood into the zone 45 comprising the upper chamber of the apparatus 10.

Referring now to FIG. 4, the apparatus 10 is shown in the blood processing mode. It will first be understood that the apparatus of FIG. 1 and the apparatus of FIG. 4 are the same apparatus, but certain components are shown differently adjusted or situated in FIG. 4 than in FIG. 1, in order to demonstrate the manner in which the apparatus works in the blood processing mode, as distinguished from the blood collecting mode. Additionally, a number of other components are shown in the illustration of FIG. 4, wherein blood discharge containers, saline inlet containers, etc. are provided, schematically demonstrating the manner in which such components cooperate with the apparatus 10 during the blood processing operation.

For processing blood, the blood inlet line 16 is removed from the port 15 and the port 15 may then be preferably closed by means of any closure, cap, or the like (not shown in FIG. 4) to protect against invasion of dust, bacteria or the like. The partial vacuum draw conduit 21 is removed from its port 20, in which it was used for the blood fill mode of operation, and the conduit 21 is placed over vacuum port 60, for drawing a partial vacuum (generally at hospital line pressure; namely 300–500 mm Hg) on regulator switch 61. While switch 61 actually functions as a switching mechanism, for discontinuing pumping of blood past the membrane, as will be discussed hereinafter, its construction is like that of a regulator, whereby the partial vacuum provided via line 21 draws against a flexible diaphragm 62 to draw a vacuum via lines 63 and 64 and to lower chamber 65 beneath the pump housing 66.

The partial vacuum provided via line 21 is greater than the opposing atmospheric vent provided via line 68, such that a net partial vacuum is established in chamber 65. This partial vacuum in lower chamber 65 causes the flexible diaphragm 67 to be drawn upwardly and to seat against diaphragm seat 70, thereby creating a reduced pressure in pump chamber 71 therebeneath which causes blood to be drawn from upper chamber 45 down through the generally semi-cylindrical vertical membrane zone 72, shown in FIG. 4, but shown more clearly in FIG. 5, with such blood then being drawn into the pump chamber 71 as shown in FIG. 4 via the open arcuate channel bottom 99 on each side of the waste discharge conduit 94 and throughout the almost 180° of arcuate open channel bottom behind the conduit 94 in FIG. 4, as shown in FIG. 5. While this is taking place, it will be understood that the diaphragm 67 stretches in that it is clamped around its periphery as at 73.

The partial vacuum draw via line 64 thus acts on the pump diaphragm 67, stretching the same to draw blood into the zone 71 as aforesaid.

As the pump diaphragm 67 reaches its terminal uppermost position, the upper central portion thereof seats against the seat 70 thereby interrupting the upward diaphragm motion and consequent downward flow of blood through the arcuate vertical membrane channel 72. When the pump diaphragm 67 seats at 70, chamber 65(a) no longer communicates with partial vacuum from line 21.

At this point, atmospheric air via vent 68 permits the stretched diaphragm 67 to retract from its fully stretched position, to resume downward movement, whereby the pressure in zone 71 increases and some of the blood that had previously been drawn into zone 71 via arcuate membrane channel 72, is pumped back, upwardly through the membrane channel 72, back into the upper chamber 45.

The force of the retracting diaphragm exceeds the suction force on the diaphragm at seat 70, and the diaphragm snaps off the seat 70, and the cycle repeats.

Thus, the back-and-forth or oscillating motion of the blood through the vertical membrane conduit 72 is effected, as a reciprocating motion, due to the alternately controlling forces; namely the vacuum draw via line 64, until it is interrupted by the diaphragm seating against the seat 70, and then the retracting force provided by the stretched diaphragm 67, after the vacuum is interrupted when the diaphragm 67 seats against the seat 70, in conjunction with atmospheric air flow at 74. Certain additional features enhance the utility of the pumping means as a novel device. The housing 66 is shaped as a partial funnel; i.e., sloped downwardly and leftwardly as seen in FIGS. 1 and 4, to minimize the volume of blood necessary to operate as a blood processing unit. The space 65 can serve as a suction reservoir. Also, the pump frequency and pressure profile can be tuned, or modified, as by changing the relative dimensions of the ducts or lines 64, the cross-sectional opening of the seat 70, the cross-sectional size of the vent 68, the relative position of the diaphragm 67, and/or the durometor hardness or stiffness of the diaphragm 67, the amount of preloading by stretching caused by the dome shaped cap 13, etc. Also, it will be noted that the inverted shape of the bottom cap 13 serves to minimize the volume of blood that is necessary for operation, by minimizing the volume of blood within the zone 71. Also, it will be seen from the above that the pump mechanism is self priming, and is tolerant to entrained air. The pump mechanism is therefore potentially useful in numerous applications for removing or delivering fluids with a partial vacuum as the driving force, for the flexible drive member provided as the diaphragm 67, for effecting relative motion between the blood and the membranes.

The diaphragm 67 thus separates the pump into a driving side 65a with which vent 68 communicates and a driven side 71, for causing oscillation of the fluid along membrane surfaces.

It will be noted that, with particular reference to FIG. 5, the channels 72 communicates with the upper chamber 45, at its upper end, and with the pump chamber 71 at its lower end.

With reference to FIG. 5, the membrane channels 72 are seen as encompassing approximately 180°, or one-half of an annular channel, and houses a membrane sandwich that functions to separate retentate components of the blood from filtrate components of the blood. Generally, as used hereout, the components of the blood that are referred to as filtrate components, will be discharged across the membranes to waste, when the filtrate components are undesirable. Such components would ordinarily include surgical irrigants, pharmaceuticals, extracellular proteins, bile, gastric fluids, fat liquids and perhaps sub-micron sized fat particles, cellular debris, blood clots, clumped cells, tissue, coagulation byproducts, cancer cells or other potentially harmful substances. The retentate components of the blood will generally include red blood cells, some platelets and perhaps some white blood cells. In some instances the filtrate components will also be usable.

With reference to FIG. 5 it will be seen that there are two discrete membrane assemblies 74 and 75, each containing multiple layers as will be described hereinafter, and doubled back on itself at 76 and 77, respectively.

As the pumping action provides vertical blood flow upwards and downwards through the membrane conduit 72, it will be seen that blood flows upwardly and downwardly, as diagrammatically indicated at 78 and 80, respectively, in each of vertical blood flow zones 81, 82, 83, 84 and 85. In between the vertical blood flow zones 81–85 are vertical membrane separation zones 86, 87, 88, and 90, wherein blood that is comprised of the filtrate components has passed through the membrane walls into said zones 86, 87, 88 and 90, for delivery into a vertically disposed waste or other blood collection zone 91, having a discharge conduit 94, for delivery to a collection bag 95. In certain clinical applications, for example for use in the processing of donor blood, the fluid collected via line 94 may be clinically useful and could collect into an appropriate receptacle for subsequent infusion. Filtrate collection line 94 is optimally configured to provide 2 to 4 feet of fluid suction head across membrane assemblies 74 and 75. This provides the transmembrane pressure which, in conjunction with the back-and-forth motion of blood along the membrane surface, enables filtrate fluid flow to filtrate collection bag 95. From time to time, one might also raise the line 94, to provide back flushing for the membrane stack due to the pressure or head that would be created by raising the line 94 in elevation.

With particular reference to FIG. 6 an enlarged detail view fragmentally illustrates the membrane stack in greater detail.

With reference now to FIG. 6, there is shown a cross-section of the membrane array, with the various layers being shown generally horizontally disposed. It will be understood that FIG. 6 is an enlarged fragmentary schematic representation and, because of the small section of detail that is enlarged, the various layers of the array would be partially curved (concave as viewed from above in the illustration of FIG. 6), if one were looking at a complete non-fragmentary illustration for the array.

In FIG. 6, as with the illustration of FIG. 5, it will be seen that, between the walls 79 and 89 that comprise the opposite sides of the arcuate channel 72, as blood is pumped vertically backward and forward (up and down) through the channel 72, such as is diagrammatically illustrated at 78 and 80, with the symbol 78 being the symbol for blood being pumped vertically upwardly, as one looks downwardly along the section line V—V of FIG. 4, and with the symbol 80 being the symbol for blood being pumped downwardly as one looks downwardly along the section line V—V of FIG. 4. Membrane layer 101 separates vertical retentate blood passageway 81 from filtrate blood conduit 86. Membrane 102 separates filtrate blood conduit 86 from vertical retentate blood passageway 82. Membrane 103 separates vertical retentate blood passageway 82 from filtrate blood conduit 87. Membrane 104 separates filtrate blood conduit 87 from vertical retentate blood passageway 83. Membrane 105 separates vertical retentate blood passageway 83 from filtrate blood conduit 88. Membrane 106 separates filtrate blood conduit 88 from vertical retentate blood passageway 84. Membrane 107 separates vertical retentate blood passageway 84 from filtrate blood conduit 90. Membrane 108 separates filtrate blood conduit 90 from vertical retentate blood passageway 85.

Screens 110 are disposed in vertical blood passageways 86, 87, 88 and 90, to separate the membranes on each side of the screens 110 and to provide a space and flow path for filtrate components of the blood that have passed through micropores (not shown) in membrane walls, in the directions of arrows 111, for example for delivery of such filtrate components to the filtrate discharge line 94. The screens 110 therefore keep the membranes on each side spaced apart to facilitate the flow of filtrate components of the blood.

Instrates 112 are disposed between the membranes 108, 101 and their associated channel walls 89, 79, respectively, and between adjacent membranes 106, 107, 104, 105 and 102, 103. The instrates 112 also serve as spacers for adjacent membranes, or between membranes and channel walls 79, 89, depending upon where the instrates 112 are located, to act as spacers to keep adjacent membranes open, away from each other, or in the case of a membrane and a wall, to keep the membrane away from the adjacent wall. The instrates 112 essentially break up the vertical channels 81, 82, 83, 84 and 85 into a great many vertical sub-channels as shown, and facilitate the creation of turbulence to the reciprocating flow of blood, to assure ample contact between the back-and-forth vertical flow of blood and the membranes, along the membrane surfaces. An optimum membrane spacing between membranes would be greater than 800 $\mu$m.

Typical membrane construction is a polyvinyl difluoridine (PVDF) polymer with an effective pore diameter of 0.45 microns. This membrane is treated with a hydrophilic coating. Other materials and pore sizes can be effective, including nylon, cellulose acetate, polycarbonate or polysulfone with pore sizes ranging from 0.2 to 2 microns.

The membrane itself may be treated to optimally pass or hold back substances as can the filter/membrane combination, as desired.

As can be seen from above, filtrate blood from the discharge conduits 86, 87, 88, and 90 is therefore delivered via line 94, to a filtrate container 95, which will gradually accumulate the filtrate components of blood until the bag or other container 95 is filled. It will be noted that the filtrate container 95 will ordinarily have graduations 114 thereon, to readily visually ascertain the volume of filtrate components of the blood accumulated in the container 95.

It will be apparent from the above that the screens 110 may be of any desirable geometric shape and may comprise a mesh, grid or the like, comprising not only the vertical components thereof shown, but generally also horizontal or other angularly disposed components (not shown), as with a conventional screen or mesh. Similarly, the instrates 112 may take on various geometric constructions as may be desired.

It is also apparent that all of the blood is pumped along the membrane array in a back-and-forth fashion. Another approach would be to provide a one-way valve at the inlet or outlet of the array and a separate supply conduit to pump chamber 67 with or without its own one-way valve. Such an arrangement would change the characteristics of flow in the array from back-and-forth to completely unidirectional or a combination thereof, although a to-and-fro motion appears to help clear the membrane.

As the blood is processed as described above, via the back-and-forth vertical pumping action through the membrane array, the volume of blood being treated within the zone 45 will be reduced as container 95 fills. In order to keep the remaining blood from becoming too thick, a replenishment liquid of various types may be added to the blood in amounts corresponding to the amount of filtrate that is withdrawn into container 95. It is possible to vary and control the amount of concentration.

Preferably, such replenishment liquid may be water in some form, most preferably as a saline solution, for example, within the range of 0.8% to 1.0% NaCl. It will be understood that "replenish" herein means the provision of a replacement liquid, with or without first concentrating the volume of liquid and can be done either partially or completely. In accordance with this invention, first concentrating the blood has shown to have substantial advantage in processing. However, the processing can include concentrating the blood and replenishing some or all of the removed components of the blood before, after, or during the concentration process. The present system allows for processing for an indefinitely long period of time with essentially no loss of red blood cells. The replenishment can take place over an indefinitely long period, until one approaches 99.999% removal of filtrate components from the blood. Such filtrate components removed can be undesirable components, such as cancer cells, pryons or the like, or other undesirable components.

The saline solution is added from a saline bag 116 (FIG. 4), preferably suitably hung via hanger 117, from a suitable location, with the bag 116 having graduations 118 thereon, for providing a visual indication of the amount of saline solution to be provided into the container 10. The saline solution may be provided to the container through a suitable spike port 120, and into line 121 past normally closed vent 122. The presence of saline in line 121 will normally hold the vent 122 closed, but when saline is no longer present in the line, such as when the amount provided from the bag 116 is exhausted into the container 10, the vent 122 opens. This type of vent 122 is conventional, and is not a part of this invention, except to the extent that it is used in combination with other features as is discussed herein. In this regard, the vent 122 acts as a switch to open or close the line 121 to air.

As saline passes through the line 121, it is delivered to the regulator-type switch means 61 as shown in FIG. 2, to come into contact with another membrane switch 123, which, like the vent closure 122 discussed above, operates such that the wet presence provided by saline solution in line 121 against the membrane switch 123 allows the vacuum drawn via partial vacuum draw line 21 to draw air through the lines 63 and 64, as aforesaid.

When saline solution is in line 121, the saline solution thus communicates along the membrane 123, to supply saline to line 125.

When the apparatus 10 of this invention is being set into a processing mode, and it is desired to provide saline solution or other replenishment liquid to the blood being treated in the zone 45, a pointer 126 carried on a bracket 127 of float lift rod 128 is moved vertically, to move the pointer 126 from the position therefor illustrated in FIG. 1, in which it is not in use, and in which the float pivot housing 130 is in its lowermost position as shown in FIG. 1, In this lower-most position the float 131 and float arm 132 which carries the float 131 are, also in their lowermost position, against the upper surface of pump housing 66, as shown in FIG. 1. Upon movement of pointer 126 from the position therefor illustrated in FIG. 1 to that of FIG. 4, along measurement graduations 133 at the side of container 10 as shown in FIG. 4, it will be seen that a numerical setting may be made that relates the placement of the pointer 126 at measured graduations to the amount of concentration to be effected, as saline solution is added to the blood from bag 116. Upon lifting the bracket 127 as shown in FIG. 4, the rod 128 also is lifted, to, in turn, lift the float pivot housing 130 as shown in FIG. 4, such that the float 131 will be lifted to correspond to a desired position from which it can maintain the liquid level 134 within chamber 45, on a generally continuous, but periodic basis, such that, as the liquid level 134 tends to drop, the corresponding downward pivoting of the float 131 will cause the arm 132 to pivot about the pivot point 135, such that the ball actuation foot 136 will cause a ball 137 to be pushed upwardly within ball housing 138, to unseat the ball, functioning as a valve, to allow saline or other replenishment liquid from line 125 to pass into the zone 45. When sufficient saline has passed into the zone 45, such that the float 131 returns to its originally set level, the valve provided by ball 137 and its actuator 136 will again close, shutting the supply of saline via line 125, until the liquid level within the zone 45 is again reduced in amount sufficient to call for the float 131 to again actuate the ball valve as aforesaid. Thus, the saline is substantially continuously, although intermittently, added to the blood within the zone 45 until the supply from container 116 is exhausted, which amount will be known not only from the graduations 118 on the container 116, but also from the graduations 133 that were pre-set upon the placement of the pointer 126 as discussed above.

When the saline supplied via container 116 is exhausted, air will enter the vent 122, and when it reaches membrane switch 123, which switch 123, being hydrophobic and thereby shedding water, will allow the diaphragm 63 to expand to contact seat 69, shutting off suction provided line 64 and thereby shutting down the pumping action that has been provided by delivery of vacuum via line 64 to lower chamber 45. It will be seen that the volume of saline used is proportional to the removal efficiency of the system and that the system will allow saline flow for as long as is clinically required to achieve optimal replenishment of waste materials. An optimal method of processing is to concentrate the collected blood to a hematocrit; for example, 40–50%, and then begin replenishment with saline. Alternately, concentrate can follow replenishment or they can occur simultaneously.

It will be noted that graduations 140 are also provided on the container 10, for example, as shown on the left side thereof, to give a visual numerical reading of the level 134 of blood being processed within the zone 45, if desired, as shown at the left of FIG. 4.

After completion of blood processing, clamping seal 141 may be removed from processed blood discharge line 142, to discharge blood into a suitable bag or other container 143, also with graduations 144 preferably being shown thereon, to give an indication of the amount of processed blood within the container 143. It will be noted that the container 143 is shown in phantom, in that it need not always be attached to the discharge line 142, but would be so attached via a suitable spike port or the like, at the time that it is desired to discharge blood from the line 142 into a container 143. The thus processed blood in the container 143 may then be re-transfused to a patient, or saved for later re-use.

With reference to FIG. 2 it will be seen that the screw or other threaded member 33 provides an external means for sealing the orifice 30 to facilitate collection when air venting is not encountered, such as from a sealed collection chamber, or a closed body cavity, such as a body cavity of a patient. In such a case, blood may be directly delivered via line 16 using vacuum via line 31 to deliver blood into the chamber 32 and then to 45.

It will be noted from FIG. 2 that an interlock bar 146 is carried on rod assembly 128, which fits over the vacuum draw port 20 as shown in FIG. 2, shown with the interlock bar 146 in its lower-most position, with the float 131 seated as shown in FIG. 1, such that the vacuum draw conduit 21 will fit on the port 20. When the system is re-set from the collection mode to the processing mode, as shown in FIG. 4, with the float 131 in a raised position as shown, the left-most end 147 of the interlock bar will prevent accidental engagement of the vacuum draw line 21 onto the vacuum draw port 20, because in the processing mode, the vacuum draw line 21 should be disposed over the vacuum draw port 60, as shown in FIG. 4.

Also, with reference to FIG. 2, it will be seen that when the interlock bar 146 is in the lower-most position as shown, the slot 148 in rod 128 is arranged such that when the rod 128 is in its fully depressed position as shown, room air is free to enter slot 148, and into line 64, to stall the pump when the interlock 147 is fully seated, so that no vacuum can inadvertently be drawn via vacuum draw port 60 when the apparatus is in the collection mode. However, when the rod 128 is lifted, the lower edge 150 of slot 148 is raised sufficiently that the slot 148 does not communicate with horizontal channel 63.

With reference to FIG. 4 it will be seen that a permanent vent 151 is provided in saline line 125, again with a hydrophobic surface to allow any air that may be present in the saline solution out of the line, but not into the line 125. Otherwise, the presence of air in the line 125 might trip the switch 123.

Various other modifications may be included with the apparatus of this invention. Optionally, a source of anticoagulant, such as heparin or acid citrate dextrose (ACD) or other liquid may be provided from a receptacle (not shown) either independently, or also via line 16 via a conjoined connection at the lower end of a wand, in instances where anticoagulant or other substances desired to be supplied to the blood prior to its delivery to the container 10.

It will be apparent from the foregoing that various other modifications may be made in the details of construction, as well as in the use and operation of the device and system in accordance with this invention, all within the spirit and scope of the invention as defined in the appended claims.

What is claimed is:

1. Apparatus for processing blood comprising: a container for receiving blood to be processed; blood inlet port means on the container for passage of blood to the container; a reservoir in the container for holding blood; a membrane protection means in the container for protecting membrane separation means from fats or other potentially harmful materials in the blood; membrane separation means for separating filtrate components of blood from retentate components of blood; pumping means disposed within the container for pumping blood past the membrane separation means; and replenishment means for at least partially, automatically replacing filtrate components of the blood with a replenishment liquid.

2. The apparatus of claim 1, wherein the membrane separation means includes means for concentrating the retentate components of the blood.

3. The apparatus of claim 1, wherein the membrane protection means comprises a filter.

4. The apparatus of claim 1, wherein the membrane protection means comprises a lipophilic fat filter.

5. The apparatus of claim 1, including partial vacuum draw port and vacuum regulator means associated with the container for regulating the level of vacuum in the container.

6. The apparatus of claim 5, wherein said partial vacuum draw port means comprises first and second partial vacuum draw ports; said first partial vacuum draw port being adapted for use in drawing blood into the container and said second partial vacuum draw port being adapted for use in operating said pumping means.

7. The apparatus of claim 6, including vacuum regulator means operably connected to said second vacuum draw port for controlling the level of vacuum delivered to said pumping means.

* * * * *